(12) United States Patent
Carvalho et al.

(10) Patent No.: US 6,818,435 B2
(45) Date of Patent: Nov. 16, 2004

(54) MICROFLUIDICS DEVICES AND METHODS FOR PERFORMING CELL BASED ASSAYS

(75) Inventors: Bruce L. Carvalho, Watertown, MA (US); Norman F. Sheppard, Jr., Bedford, MA (US); Christina Feakes, Brighton, MA (US); Gregory J. Kellogg, Cambridge, MA (US)

(73) Assignee: Tecan Trading AG (CH)

( * ) Notice: Subject to any disclaimer, the term of this patent is extended or adjusted under 35 U.S.C. 154(b) by 297 days.

(21) Appl. No.: 09/858,558

(22) Filed: May 15, 2001

(65) Prior Publication Data

US 2002/0106786 A1 Aug. 8, 2002

Related U.S. Application Data

(60) Provisional application No. 60/204,264, filed on May 15, 2000.

(51) Int. Cl.[7] .................................................. C12M 1/36
(52) U.S. Cl. .................... 435/286.5; 435/286.7; 435/287.2; 435/287.3; 435/288.7
(58) Field of Search ................... 422/64; 435/286.5, 435/286.7, 287.2, 287.3, 288.7

(56) References Cited

U.S. PATENT DOCUMENTS

| | | |
|---|---|---|
| 4,675,285 A | 6/1987 | Clark et al. |
| 4,760,067 A | 7/1988 | Firestone |
| 5,166,322 A | 11/1992 | Shaw et al. |
| 5,446,090 A | 8/1995 | Harris |
| 5,569,779 A | 10/1996 | Sabahi et al. |
| 6,063,589 A | 5/2000 | Kellogg et al. |

FOREIGN PATENT DOCUMENTS

| | | |
|---|---|---|
| GB | 2 341 924 A | 3/2000 |
| WO | WO 97/21090 A1 | 7/1997 |
| WO | WO 98/07019 A1 | 2/1998 |
| WO | WO 98/28623 A1 | 7/1998 |
| WO | WO 99/55827 A1 | 11/1999 |

OTHER PUBLICATIONS

Brody et al., "Biotechnology at Low Reynolds Numbers", Biophysical Journal, Dec. 1996, 71:3430–3441.

Duffy et al., "Microfabricated Centrifugal Microfluidics Systems: Characterization and Multiple Enzymatic Assays" Anal. Chem. 1999, 71:4669–4678.

*Primary Examiner*—David A. Redding
(74) *Attorney, Agent, or Firm*—McDonnell Boehnen Hulbert & Berghoff

(57) ABSTRACT

This invention provides methods and apparatus for performing microanalytic analyses and procedures, particularly miniaturized cell based assays. These methods are useful for performing a variety of cell-based assays, including drug candidate screening, life sciences research, and clinical and molecular diagnostics.

26 Claims, 10 Drawing Sheets

MICROFLUIDICS DEVICES AND METHODS FOR PERFORMING CELL BASED ASSAYS

This application claims priority to U.S. Provisional Application Ser. No. 60/204,264, filed May 15, 2000, the disclosure of which is explicitly incorporated by reference herein.

BACKGROUND OF THE INVENTION

1. Field of the Invention

This invention relates to methods and apparatus for performing microanalytic analyses and procedures. In particular, the present invention provides devices and methods for the performance of miniaturized cell based assays. These assays may be performed for a variety of purposes, including but not limited to screening of drug candidate compounds, life sciences research, and clinical and molecular diagnostics.

2. Background of the Related Art

Recent developments in a variety of investigational and research fields have created a need for improved methods and apparatus for performing analytical, particularly bioanalytical assays at microscale (i.e., in volumes of less than 100 $\mu$L). In the field of pharmaceuticals, an increasing number of potential drug candidates require assessment of their biological function. As an example, the field of combinatorial chemistry combines various structural sub-units with differing chemical affinities or configurations into molecules; in theory, a new molecule having potentially unique biochemical properties can be created for each permutation of the sub-units. In this way, large libraries of compounds may be synthesized from relatively small numbers of constituents, each such compound being a potential drug lead compound of usually unknown biological activity and potency. Similarly, increasingly large numbers of targets for these putative therapeutic compounds are being discovered, many as a result of the growing information derived from such large-scale biological research as the sequencing of the human genome.

As the first phase of drug discovery, compounds that represent potential drugs are screened against targets in a process known as High Throughput Screening (HTS) or ultra-High Throughput Screening (uHTS). An advantage of these screening methods is that they usually consist of simple solution phase biochemical assays that can be performed quickly and with small amounts of expensive compounds and reagents. However, a significant drawback to HTS is that the targets do not provide a functional assessment of compounds' effects on the complex biochemical pathways inherent in the normal and abnormal (mutant or disease-state) functioning of cells, tissues, organs, and organisms. As a result, compounds that have shown biochemical activity of interest in initial screens are usually put through cell-based screens, in which the affect of the compounds on cellular function is independently assayed.

There are a wide range of assays that may be performed using living cells. Assays that involve the use of living cells include gene expression, in which levels of transcription in response to a drug candidate are monitored; cell permeability assays, in which the ability of drugs to traverse membranes of cells is monitored; and functional assays designed to investigate both macroscopic effects, such as cell viability, as well as biochemical effects and products produced in and by the cells as a result of treatment with the drug lead compound.

These assays include cytotoxicity and cell proliferation to measure the viability of a population of cells, often in the presence of a putative therapeutic compound (drug candidate). A variety of methods have been developed for this purpose. These include the use of tetrazolium salts, in which mitochondria in living cells use dehydrogenases to reduce tetrazolium salts to colored formazan salts. Soluble or insoluble precipitates may be formed, depending on the nature of the tetrazolium salt used. A typical assay procedure is to culture the cells, add a solution of tetrazolium salt, phenazine methosulfate and DPBS, incubate, and determine absorbance at 490 nm. The absorbance measured is larger for viable cell populations that have metabolized the salt. Another such assay uses alamarBlue, which uses a fluorometric/colorimetric growth indicator that is reduced to a membrane-soluble, red, fluorescent form by the products of metabolic activity. A variety of other indicators are either taken up by living cells, dead cells, or both; for example, neutral red is taken up only by live cells, while trypan blue is excluded by live cells. Dyes that bind to or intercalate with DNA can be used to visualize or quantitate the number of live or dead cells, since DNA synthesis only occurs in living cells.

Another important class of cell based assays in reporter gene assays. These assays are used to study the control of gene transcription. They can also be used as a secondary detection method for a number of other molecules present in or acting on a cell. Pharmaceutical companies and others involved in drug development commonly utilize reporter gene assays to determine the effects of their compounds on transcription of specific genes whose promoter sequences are known. For example, the production of proteins associated with a condition of interest can be quantified by using a reporter gene operatively linked to the promoter of the gene encoding the protein. The method employed in reporter gene assays varies with the type of reporter gene used and the application. Initially, the promoter from the gene of interest in operable combination with the reporter gene is inserted into a commercially available plasmid comprising an antibiotic resistance gene, which is then transfected into the cells. Cells that have been successfully transfected can be selected by addition of the antibiotic, thereby eliminating the cells that have not been successfully transduced with the plasmid. When studying gene transcription, the cells are subsequently plated, compound(s) to be tested are introduced, and the assay for the reporter protein is conducted. These assays range from extremely simple to complex, with reporter proteins ranging from enzymes to hormones and photoproteins. Typically, enzymes are assayed using rate assays, hormones are detected using immunoassays, and photoproteins (e.g., green fluorescent protein, aequorin) are imaged optically.

Cell permeability assays measure the transport of compounds across cells. The commonly-used example is the CaCo-2 cell line derived from human intestinal endothelial cells. When grown to confluency over a porous membrane, these cells form a "biologically active" filter: Transport of compound through the cell layer is accepted in the art to be correlated with absorbsion by the digestive system.

The compounds available for such cell-based testing have increased dramatically in recent years. In the decade from 1985 to 1995, drug library development through methods such as combinatorial chemistry and the discovery of new targets have created an explosive growth in both the number of compounds with promising biochemical properties. In order to effectively assay these "hits" using cell-based assays, an equivalent system of high throughput screening for such cell-based assays is needed.

To achieve the primary need of high throughput for cell based assays, a number of secondary features are desirable.

First, it is advantageous to have a high degree of process automation, such as fluid transfer, cell plating and washing, and detection. It is also advantageous for the processes to be integrated so as to require a minimum of human intervention. Compound consumption (non-specific adsorption onto the materials comprising the assay apparatus) must be minimized, in order to prevent depletion of rare and/or expensive components of the compound libraries. This is most readily addressed through miniaturization of assays from their current scale of hundreds of microliters to ten microliters or less. A goal in the art is to provide automated, integrated and miniaturized apparatus for performing assays that are reliable and produce results consistent with the results produced by current, more laborious, expensive and time-consuming assays.

In addition to these advantages, miniaturization itself can confer performance advantages. At short length scales, diffusionally-limited mixing is rapid and can be exploited to create sensitive assays (Brody et al., 1996, *Biophysical J*. 71: 3430–3431). Because fluid flow in miniaturized pressure-driven systems is laminar, rather than turbulent, processes such as washing and fluid replacement are well-controlled. Miniaturized, most advantageously microfabricated systems also enable assays that rely on a large ratio of surface area to volume, such chromatographic assays generally and assays that require binding to a surface.

Miniaturization has led to the creation of 384-well and 1536-well microtiter plates for total reaction volumes of between 0.015 and 0.1 mL. However, a number of problems arise when miniaturizing standard plate technology, especially for use in conjunction with cells. First, because the total volumes are smaller and the plates are open to the environment, evaporation of fluid during the course of an assay can compromise results; this is especially problematic for cell based assays that may require incubation at elevated temperatures for up to several days. Another drawback of open plates is the existence of the meniscus of fluid in the well. Menisceses of varying configurations (due, for example to imperfections in the plate or differences in contact angle and surface tension) can distort the optical signals used to interrogate the samples. As the strength of the optical signals decreases with decreasing assay volume, correction for background distortions becomes more difficult. Finally, optical scanning systems for high-density plates are often complex and expensive. Methods that minimize evaporation, provide a more uniform optical pathway, and provide simpler detection schemes are desirable.

Highly accurate pipetting technologies have been developed to deliver fluids in precisely metered quantities to these plates. Most of these fluid-delivery methods for low volumes (below approximately 0.5 $\mu$L) rely on expensive piezoelectric pipetting heads that are complex and difficult to combine or "gang" into large numbers of independent pipettors so that many wells may be addressed independently. As a result, fluid delivery is either completely or partially serial (i.e., a single micropipettor, or a small number of parallel delivery systems used repeatedly to address the entire plate). Serial pipetting defeats the aim of parallelism by increasing the amount of time required to address the plate. Methods that reduce the number and precision of fluid transfer steps are therefore needed.

Attempts to produce microfabricated devices for performing cell-based assays have been reported in the art. For example, International Patent Application WO98/028623, published 2, Jul. 1998 by several of the instant inventors, discloses a microfluidics platform for detecting particulates in a fluid, specifically including cells.

A microfabricated device explicitly for the performance of cell based assays in a centrifugal format has been disclosed in International Patent Application WO 99/55827, published November 1999. The operative principles of this device include the use of hydrophobic coatings along a radial channel punctuated by cell culturing chambers and optical cuvettes. However, this device cannot perform distinct assays on subpopulations of the cells cultured on the device. By providing only a single entry to a multiplicity of cell culturing chambers, all chambers are exposed to the same solutions, such as cell suspension, cell culture medium, test compounds and any reagents used for detection of the effects of these compounds. Furthermore, the format disclosed in WO 99/55827 relies on the manufactured surface of the microplatform to provide the support for cell attachment and proliferation, or the use of carrier beads. This may not be adequate for all cell types of interest. Finally, no provision is made for selectively trapping and incubating certain cells or cell types rather than others. In applications such as diagnostics, in which a variety of cells may be present in a biological sample such as blood, means for separating cells based on type or other features may be required.

Thus, there is a need in the art for improved micromanipulation apparatus and methods for performing cell based assays more rapidly and economically using less biological sample material. Relevant to this need in the art, some of the present inventors have developed a microsystem platform and a micromanipulation device to manipulate said platform by rotation, thereby utilizing the centripetal forces resulting from rotation of the platform to motivate fluid movement through microchannels embedded in the microplatform, as disclosed in co-owned U.S. Pat. No. 6,063,589, issued May 16, 2000, and co-owned and co-pending patent application U.S. Ser. Nos. 08/761,063, filed Dec. 5, 1996 now abandoned; 08/768,990, filed Dec. 18, 1996 now U.S. Pat. No. 6,319,469; 08/910,726, filed Aug. 12, 1997 now U.S. Pat. No. 6,143,248; 08/995,056, filed Dec. 19, 1997 now U.S. Pat. No. 6,143,243; and 09/315,114, filed May 19, 1999 now U.S. Pat. No. 6,632,399, the disclosures of each of which are explicitly incorporated by reference herein.

SUMMARY OF THE INVENTION

The invention disclosed herein relates to microfluidic devices for performing cell based assays for a variety of applications such as life sciences, diagnostics and drug screening. In particular, these devices have been developed to carry out various steps common to many cell-based assays. The devices comprise an entry port or other means for adding cellular suspensions, most preferably in vitro cell cultures, into the devices of the invention. Surfaces and supports comprising the devices have been adapted or treated to permit cell attachment and growth to occur on appropriate surfaces and supports in the devices, while alternatively other surfaces or components of the devices have been fabricated or treated to inhibit cell attachment and growth. The components of the devices are arranged to permit cell growth on the surface of the device, including such attendant process as exchange of growth media, exchange of gases like carbon dioxide naturally respired during growth, and incubation at temperatures appropriate for cell culture. The devices of the invention are produced to facilitate distribution of test solutions to the cells cultured within the device, said solutions preferably carrying test compounds or other reagents. Finally, the components of the devices of the invention are provided so that metabolites, secretions, or excretions from cells on the device can be detected, either directly or through reaction with appropriate reagents. Another preferred form of detection provided is the direct visualization and imaging of cells.

This invention provides microsystems platforms as disclosed in co-owned U.S. Pat. No. 6,063,589, issued May 16, 2000, and co-owned and co-pending patent application U.S. Ser. Nos. 08/61,063, filed Dec. 5, 1996; 08/768,990, filed Dec. 18, 1996; 08/910,726, filed Aug. 12, 1997; 08/995,056, filed Dec. 19, 1997; and 09/315,114, filed May 19, 1999, the disclosures of each of which are explicitly incorporated by reference herein, adapted to permit cell attachment and growth on the surface thereof, most preferably in specific components such as cell growth chambers as described herein. Additional microfluidics components that facilitate the performance of cell based assays are also provided, as described in more detail herein.

The invention provides apparatus and methods for performing microscale processes on a microplatform, whereby fluid is moved on the platform in defined channels motivated by centripetal force arising from rotation of the platform. The first element of the apparatus of the invention is a microplatform that is a rotatable structure, most preferably a disk, the disk comprising fluid (sample) inlet ports, fluidic microchannels, reagent reservoirs, cell growth or aggregation chambers, detection chambers and sample outlet ports, generically termed "microfluidic structures," and also comprise heating elements that make up a portion of the surface area of the platform for heating fluids contained therein to temperatures greater than ambient temperature. In preferred embodiments, said heating elements are positioned on the disk in sufficient proximity to the cell growth or aggregation chambers to allow cell growth in said chambers on the disk surface without inhibiting cell growth or otherwise compromising the viability of growing cells. The disk is rotated at speeds from about 1-30,000 rpm for generating centripetal acceleration that enables fluid movement through the microfluidic structures of the platform. The disks of the invention also preferably comprise air outlet ports and air displacement channels. The air outlet ports and in particular the air displacement ports provide a means for fluids to displace air, thus ensuring uninhibited movement of fluids on the disk. These air outlet ports also permit gas exchange between cell growth or aggregation chambers and the atmosphere, to allow the culture media to be oxygenated and to eliminate gaseous waste such as carbon monoxide. Specific sites on the disk also preferably comprise elements that allow fluids to be analyzed, as well as detectors for each of these effectors. Alternatively, some or all of these elements can be contained on a second disk that is placed in optical or direct physical contact, most preferably thermal contact, with the first platform disk.

The discs of this invention have several advantages over those that exist in the centrifugal analyzer art. Foremost is the fact that flow is laminar due to the small dimensions of the fluid channels; this allows for better control of processes such as mixing and washing. To this are added the already described advantages of miniaturization, as described in more detail above.

The second element of the invention is a micromanipulation device that is a disk player/reader device that controls the function of the disk. This device comprises mechanisms and motors that enable the disk to be loaded and rotated. In addition, the device provides means for a user to operate the Microsystems in the disk and access and analyze data, preferably using a keypad and computer display. The micromanipulation device also advantageous provides means for actuation of on-disc elements, such active valves; the application and control of heat to the disc for purposes of chemical or biological incubation; and means for adding fluids to and removing fluids from the discs. In preferred embodiments, the apparatus also comprises means for insulating the platforms of the invention from the environment, so that cells growing on the disc can be maintained at the proper temperature, oxygen tension, acidity, humidity levels, and other parameters understood by those with skill in the cell culture arts.

The invention specifically provides Microsystems platforms comprising microfluidics components contained in one or a multiplicity of platform layers that are fluidly connected to permit transfer, mixing and assay performance on the sealed surface of the platform. The platforms preferably comprise one or more entry ports through which cell suspensions may be added in volumes ranging from about 1 nL to about 1 mL. The platforms preferably comprise one or more reagent reservoirs containing a sufficient volume, preferably from about 1 nL to about 1 mL, of a reagent solution for a multiplicity of individual assays. The reagent reservoirs are fluidly connected by microchannels to one or preferably a multiplicity of cell incubation chambers. These cell incubation chambers are preferably equipped with a surface that has been constructed or specifically adapted for attachment and growth of cells, and may also be sealed with selectively-permeable membranes for which allow passage of gases in and out of the chambers from the exterior environment. Cell incubation chambers may be equipped with devices for capturing cells passed through the chambers. Additionally, the cell incubation chambers may be fluidly connected to detection chambers and waste chambers. In some preferred embodiments, the platform comprises a multiplicity mixing channels and reservoirs for the mixing of reagents in various ratios and for the creation of dilution series for performing cell-based assays of drugs and other compounds.

In the use of the platforms of the invention, fluids (including cell suspensions and reagents) are added to the platform when the platform is at rest. Thereafter, rotation of the platform on a simple motor motivates fluid movement through microchannels for various processing steps. In preferred embodiments, the platforms of the invention permit the use of a detector, most preferably an optical detector, for detecting the products of an assay, most preferably a biochemical assay, whereby the assay reaction chambers comprise optical cuvettes, preferably positioned at the outer edge of the platform, and most preferably wherein the platform is scanned past a fixed detector through the action of the rotary motor. In other embodiments, the platforms permit the use of optical imaging systems for the direct visualization of cells that have attached to support surfaces within the platform Because the platforms of the invention are most preferably constructed using microfabrication techniques as described more fully below, the volumes of fluids used may be made arbitrarily small as long as the detectors used have sufficient sensitivity.

The present invention solves problems in the current art through the use of a microfluidic disc in which centripetal acceleration is used to move fluids. It is an advantage of the microfluidics platforms of the present invention that the fluid-containing components are constructed to contain small volumes, thus reducing reagent costs, reaction times and the amount of biological material required to perform an assay. It is also an advantage that the fluid-containing components are sealed, thus eliminating experimental error due to differential evaporation of different fluids and the resulting changes in reagent concentration, as well as reducing the risk of contamination, either of the cell culture or the operator. Because the microfluidic devices of the invention are completely enclosed, both evaporation and optical distortion are reduced to negligible levels. The platforms of the invention also advantageously permit "passive" mixing and valving, i.e., mixing and valving are performed as a consequence of the structural arrangements of the components on the platforms (such as shape, length, position on the platform surface relative to the axis of rotation, and surface properties of the interior surfaces of the components, such as wettability as discussed below), and the dynamics of platform rotation (speed, acceleration, direction and change-of-direction), and permit control of assay timing and reagent delivery.

In alternative embodiments of the platforms of the invention, metering structures as disclosed in co-owned U.S. Pat. No. 6,063,589, issued May 16, 2000 and incorporated by reference herein, are used to distribute aliquots of reagent to each of a multiplicity of mixing structures, each mixing structure being fluidly connected to one of a multiplicity of sample reservoirs, thereby permitting parallel processing and mixing of the samples with a common reagent. This reduces the need for automated reagent distribution mechanisms, reduces the amount of time required for reagent dispensing (that can be performed in parallel with distribution of reagent to a multiplicity of reaction chambers), and permits delivery of small (nL-to-$\mu$L) volumes without using externally-applied electromotive means. It also enables the performance of multiplexed assays, in which cell populations may be divided and the microfluidics of the device used to perform a variety of assays on different sub-populations in parallel, on one population serially, or on a single population simultaneously.

A further advantage of the platforms of the invention is the use of elements that can serve to selectively capture cells based on properties such as size (though the use of porous filters) or type (through the use of immunochemical methods, as disclosed in co-owned U.S. Pat. No. 6,143,247, issued 7, Nov. 2000 and International Application Publication No. WO98/28623, published 2, Jul. 1999, the teachings of each of which are explicitly incorporated by reference herein).

The assembly of a multiplicity of cell incubation chambers on the platforms of the invention also permits simplified detectors to be used, whereby each individual reaction chamber can be scanned using mechanisms well-developed in the art for use with, for example, CD-ROM technology. Finally, the platforms of the invention are advantageously provided with sample and reagent entry ports for filling with samples and reagents, respectively, that can be adapted to liquid delivery means known in the art (such as micropipettors).

The platforms of the invention reduce the demands on automation in at least three ways. First, the need for precise metering of delivered fluids is relaxed through the use of on-disc metering structures, as described more fully in co-owned U.S. Pat. No. 6,063,589, issued May 16, 2000, and co-owned and co-pending patent application U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; and 09/315,114, filed May 19, 1999, the disclosures of each of which are explicitly incorporated by reference herein. By loading imprecise volumes, slightly in excess of those needed for the assay, and allowing the rotation of the disc and use of appropriate microfluidic structures to meter the fluids, much simpler (and less expensive) fluid delivery technology may be employed than is the conventionally required for high-density microtitre plate assays.

Second, the total number of fluid "delivery" events on the microfluidic platform is reduced relative to conventional assay devices such as microtiter plates. By using microfluidic structures that sub-divide and aliquot common reagents (such as reagent solutions, buffers, and enzyme substrates) used in all assays performed on the platform, the number of manual or automated pipetting steps are reduced by at least half (depending on the complexity of the assay). Examples of these structures have been disclosed in co-owned U.S. Pat. No. 6,063,589, issued May 16, 2000, and incorporated by reference herein. In some examples shown explicitly herein, the microfluidic structures of the platform may be used to create, for example, multiple mixtures of reagents with different mixing ratios for application to cultured cells. These structures provide automation, for example, for serial dilution assays, a laborious process when performed conventionally. This process is replaced by "parallel dilution" on the platforms of the invention.

Finally, the invention also provides on-platform means for adding incubation media, washing cell incubation chambers, and media replacement. These features also reduce manipulation of the assay device by, for example, robotic washing stations, as well as providing controlled and integrated fluid processing.

Certain preferred embodiments of the apparatus of the invention are described in greater detail in the following sections of this application and in the drawings.

DETAILED DESCRIPTION OF PREFERRED EMBODIMENTS

Figure 1:
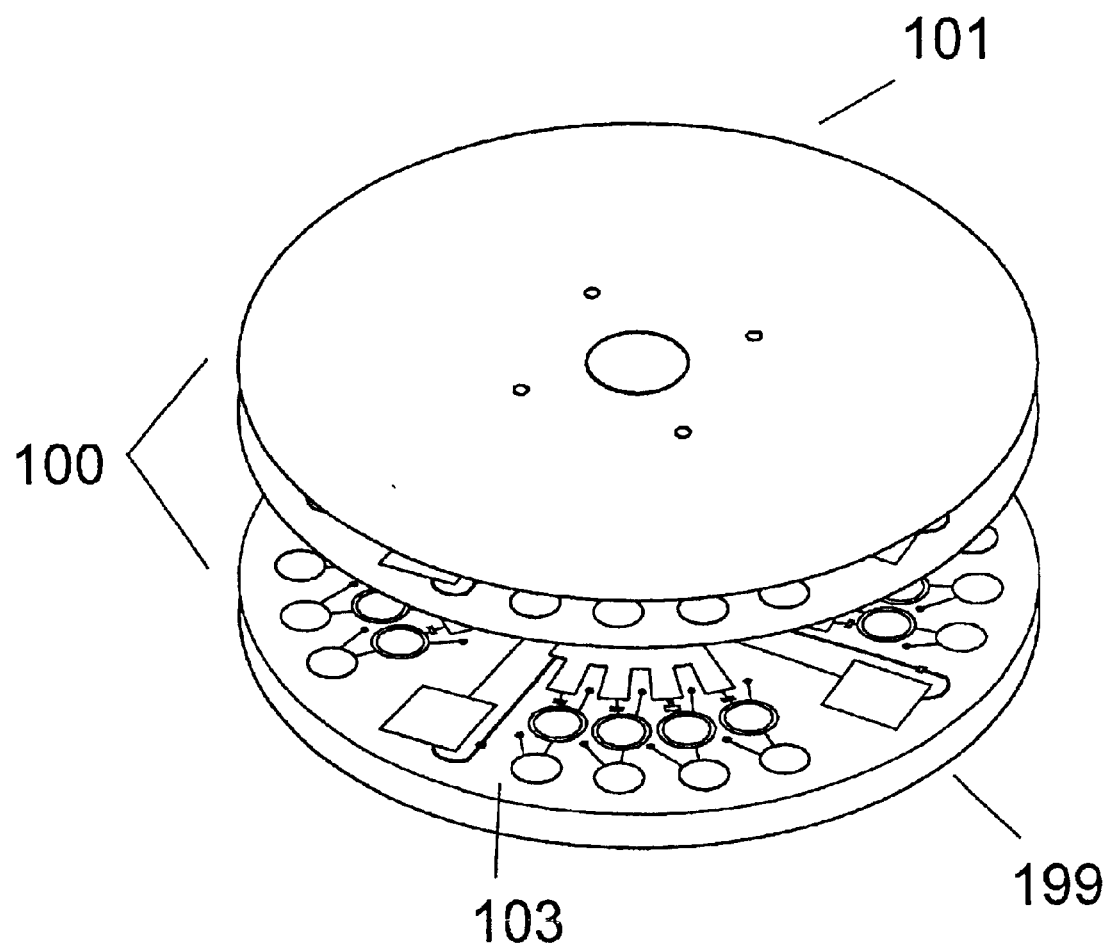
FIG. 1 depicts an oblique, exploded view of a disc developed with a flow-through membrane for capturing cells

This invention provides a microplatform and a micromanipulation device as disclosed in co-owned U.S. Pat. No. 6,063,589, issued May 16, 2000, and co-owned and co-pending patent application U.S. Ser. Nos. 08/761,063, filed Dec. 5, 1996; 08/768,990, filed Dec. 18, 1996; 08/910, 726, filed Aug. 12, 1997; 08/995,056, filed Dec. 19, 1997; 09/315,114, filed May 19, 1999, the disclosures of each of which are explicitly incorporated by reference herein, adapted for performing microanalytical and microsynthetic assays of biological samples.

For the purposes of this invention, the term "sample" will be understood to encompass any fluid, solution or mixture, either isolated or detected as a constituent of a more complex mixture, or synthesized from precursor species. In particular, the term "sample" will be understood to encompass any biological species of interest. The term "biological sample" or "biological fluid sample" will be understood to mean any biologically-derived sample, including but not limited to blood, plasma, serum, lymph, saliva, tears, cerebrospinal fluid, urine, sweat, plant and vegetable extracts, semen, and ascites fluid.

For the purposes of this invention, the term "a centripetally motivated fluid micromanipulation apparatus" is intended to include analytical centrifuges and rotors, microscale centrifugal separation apparatuses, and most particularly the Microsystems platforms and disk handling apparatuses as described in co-owned U.S. Pat. No. 6,063,589, issued May 16, 2000, and co-owned and co-pending patent application U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999, the disclosures of each of which are explicitly incorporated by reference herein.

For the purposes of this invention, the term "Microsystems platform" is intended to include centripetally-motivated microfluidics arrays as described in co-owned U.S. Pat. No. 6,063,589, issued May 16, 2000, and co-owned and co-pending patent application U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999, the disclosures of each of which are explicitly incorporated by reference herein.

In one aspect of the platforms of the invention is provided a surface or cell growth or accumulation chamber treated to comprise a specific binding reagent. For the purposes of this invention, the term "specific binding reagent" is intended to encompass biomolecules having a specific binding affinity between pairs thereof providing a specific molecular binding interaction with a binding affinity constant of between about $10^{-4}$ and $10^{-15}$ M. Examples of such pairs of specific binding reagents include but are not limited to antigen and antibody, including antisera, polyclonal antibodies and most preferably monoclonal antibodies; receptor and ligands, including cell-surface receptors; integrins and adhesion proteins, including ICAM-I and ICAM-II; and carbohydrates and lectins, including phytohemagglutinin. As provided by the invention, specific binding reagents comprising a first member of a specific binding pair is provided coating a surface or cell culture reservoir of a platform designed or intended to permit cell growth or accumulation thereupon, most preferably a cell expressing a cognate antigen, receptor or adhesion protein or having a carbohydrate moiety at the cell surface specific for a particular lectin. Said specific binding reagent is applied to the surface or cell growth or accumulation chamber of the platform by depositing the reagent on the surface using any appropriate means, including inkjet printing, computer-positioned syringes, microetching and microlithographic methods, including photolithography, screen and airbrush printing methods, solution coating, dipping, and conventional microtitre-well techniques.

For the purposes of this invention, the terms "capillary", "microcapillary" and "microchannel" will be understood to be interchangeable and to be constructed of either wetting or non-wetting materials where appropriate.

For the purposes of this invention, the term "reagent reservoir," "assay chamber," "fluid holding chamber," "collection chamber" and "detection chamber" will be understood to mean a defined volume on a microsystems platform of the invention comprising a fluid.

For the purposes of this invention, the terms "entry port" and "fluid input port" will be understood to mean an opening on a microsystems platform of the invention comprising a means for applying a fluid to the platform.

For the purposes of this invention, the terms "exit port" and "fluid outlet port" will be understood to mean a defined volume on a microsystems platform of the invention comprising a means for removing a fluid from the platform.

For the purposes of this invention, the term "capillary junction" will be understood to mean a region in a capillary or other flow path where surface or capillary forces are exploited to retard or promote fluid flow. A capillary junction is provided as a pocket, depression or chamber in a hydrophilic substrate that has a greater depth (vertically within the platform layer) and/or a greater width (horizontally within the platform layer) that the fluidics component (such as a microchannel) to which it is fluidly connected. For liquids having a contact angle less than 90° (such as aqueous solutions on platforms made with most plastics, glass and silica), flow is impeded as the channel cross-section increases at the interface of the capillary junction. The force hindering flow is produced by capillary pressure, that is inversely proportional to the cross sectional dimensions of the channel and directly proportional to the surface tension of the liquid, multiplied by the cosine of the contact angle of the fluid in contact with the material comprising the channel. The factors relating to capillarity in microchannels according to this invention have been discussed in co-owned U.S. Pat. No. 6,063,589, issued May 12, 2000 and in co-owned and co-pending U.S. patent application Ser. No. 08/910,726, filed Aug. 12, 1997, incorporated by reference in its entirety herein.

Capillary junctions can be constructed in at least three ways. In one embodiment, a capillary junction is formed at the junction of two components wherein one or both of the lateral dimensions of one component is larger than the lateral dimension(s) of the other component. As an example, in microfluidics components made from "wetting" or "wettable" materials, such a junction occurs at an enlargement of a capillary as described in co-owned and co-pending U.S. Ser. Nos. U.S. Ser. Nos. 08/761,063, filed Dec. 5, 1996; 08/768,990, filed Dec. 18, 1996; and 08/910,726, filed Aug. 12, 1997. Fluid flow through capillaries is inhibited at such junctions. At junctions of components made from non-wetting or non-wettable materials, on the other hand, a constriction in the fluid path, such as the exit from a chamber or reservoir into a capillary, produces a capillary junction that inhibits flow. In general, it will be understood that capillary junctions are formed when the dimensions of the components change from a small diameter (such as a capillary) to a larger diameter (such as a chamber) in wetting systems, in contrast to non-wettable systems, where capillary junctions form when the dimensions of the components change from a larger diameter (such as a chamber) to a small diameter (such as a capillary).

A second embodiment of a capillary junction is formed using a component having differential surface treatment of a capillary or flow-path. For example, a channel that is hydrophilic (that is, wettable) may be treated to have discrete regions of hydrophobicity (that is, non-wettable). A fluid flowing through such a channel will do so through the hydrophilic areas, while flow will be impeded as the fluid-vapor meniscus impinges upon the hydrophobic zone.

The third embodiment of a capillary junction according to the invention is provided for components having changes in both lateral dimension and surface properties. An example of such a junction is a microchannel opening into a hydrophobic component (microchannel or reservoir) having a larger lateral dimension. Those of ordinary skill will appreciate how capillary junctions according to the invention can be created at the juncture of components having different sizes in their lateral dimensions, different hydrophilic properties, or both.

For the purposes of this invention, the term "capillary action" will be understood to mean fluid flow in the absence of rotational motion or centripetal force applied to a fluid on a rotor or platform of the invention and is due to a partially or completely wettable surface.

For the purposes of this invention, the term "capillary microvalve" will be understood to mean a capillary microchannel comprising a capillary junction whereby fluid flow is impeded and can be motivated by the application of pressure on a fluid, typically by centripetal force created by rotation of the rotor or platform of the invention. Capillary microvalves will be understood to comprise capillary junctions that can be overcome by increasing the hydrodynamic pressure on the fluid at the junction, most preferably by increasing the rotational speed of the platform.

For the purposes of this invention, the term "in fluid communication" or "fluidly connected" is intended to define components that are operably interconnected to allow fluid flow between components.

For the purposes of this invention, the term "air displacement channels" will be understood to include ports in the surface of the platform that are contiguous with the components (such as microchannels, chambers and reservoirs) on the platform, and that comprise vents and microchannels that permit displacement of air from components of the platforms and rotors by fluid movement.

The microplatforms of the invention (preferably and hereinafter collectively referred to as "disks"; for the purposes of this invention, the terms "microplatform", "Microsystems platform" and "disk" are considered to be interchangeable) are provided to comprise one or a multiplicity of microsynthetic or microanalytic systems (termed "microfluidics structures" herein). Such microfluidics structures in turn comprise combinations of related components as described in further detail herein that are operably interconnected to allow fluid flow between components upon rotation of the disk. These components can be microfabricated as described below either integral to the disk or as modules attached to, placed upon, in contact with or embedded in the disk. For the purposes of this invention, the term "microfabricated" refers to processes that allow production of these structures on the sub-millimeter scale. These processes include but are not restricted to molding, photolithography, etching, stamping and other means that are familiar to those skilled in the art.

The invention also comprises a micromanipulation device for manipulating the disks of the invention, wherein the disk is rotated within the device to provide centripetal force to effect fluid flow on the disk. Accordingly, the device provides means for rotating the disk at a controlled rotational velocity, for stopping and starting disk rotation, and advantageously for changing the direction of rotation of the disk. Both electromechanical means and control means, as further described herein, are provided as components of the devices of the invention. User interface means (such as a keypad and a display) are also provided, as further described in co-owned U.S. Pat. No. 6,063,589, issued May 16, 2000, and co-owned and co-pending patent application U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; 09/315,114, filed May 19, 1999, the disclosures of each of which are explicitly incorporated by reference herein.

The invention provides a combination of specifically-adapted microplatforms that are rotatable, analytic/synthetic microvolume assay platforms, and a micromanipulation device for manipulating the platform to achieve fluid movement on the platform arising from centripetal force on the platform as result of rotation. The platform of the invention is preferably and advantageously a circular disk; however, any platform capable of being rotated to impart centripetal for a fluid on the platform is intended to fall within the scope of the invention. The micromanipulation devices of the invention are more fully described in co-owned and co-pending U.S. Ser. Nos. U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; and 09/315,114, filed May 19, 1999, the disclosures of each of which are explicitly incorporated by reference herein.

Fluid (including reagents, samples and other liquid components) movement is controlled by centripetal acceleration due to rotation of the platform. The magnitude of centripetal acceleration required for fluid to flow at a rate and under a pressure appropriate for a particular microfluidics structure on the microsystems platform is determined by factors including but not limited to the effective radius of the platform, the interior diameter of microchannels, the position angle of the microchannels on the platform with respect to the direction of rotation, and the speed of rotation of the platform. In certain embodiments of the methods of the invention an unmetered amount of a fluid (either a sample or reagent solution) is applied to the platform and a metered amount is transferred from a fluid reservoir to a microchannel, as described in co-owned U.S. Pat. No. 6,063,589, issued May 16, 2000, and co-owned and co-pending patent application U.S. Ser. Nos. 08/761,063, filed Dec. 5, 1996; 08/768,990, filed Dec. 18, 1996; 08/910, 726, filed Aug. 12, 1997; 08/995,056, filed Dec. 19, 1997; 09/315,114, filed May 19, 1999, the disclosures of each of which are explicitly incorporated by reference herein, In preferred embodiments, the metered amount of the fluid sample provided on an inventive platform is from about 1 nL to about 500 µL. In these embodiments, metering manifolds comprising one or a multiplicity of metering capillaries are provided to distribute the fluid to a plurality of components of the microfluidics structure.

The components of the platforms of the invention are in fluidic contract with one another. In preferred embodiments, fluidic contact is provided by microchannels comprising the surface of the platforms of the invention. Microchannel sizes are optimally determined by specific applications and by the amount of and delivery rates of fluids required for each particular embodiment of the platforms and methods of the invention. Microchannel sizes can range from 0.1 µm to a value close to the thickness of the disk (e.g., about 1 mm); in preferred embodiments, the interior dimension of the microchannel is from 0.5 µm to about 500 µm. Microchannel and reservoir shapes can be trapezoid, circular or other geometric shapes as required. Microchannels preferably are embedded in a microsystem platform having a thickness of about 0.1 to 25 mm, wherein the cross-sectional dimension of the microchannels across the thickness dimension of the platform is less than 1 mm, and can be from 1 to 90 percent of said cross-sectional dimension of the platform. Sample reservoirs, reagent reservoirs, reaction chambers, collection chambers, detections chambers and sample inlet and outlet ports preferably are embedded in a microsystem platform having a thickness of about 0.1 to 25 mm, wherein the cross-sectional dimension of the microchannels across the thickness dimension of the platform is from 1 to 75 percent of said cross-sectional dimension of the platform. In preferred embodiments, delivery of fluids through such channels is achieved by the coincident rotation of the platform for a time and at a rotational velocity sufficient to motivate fluid movement between the desired components.

The flow rate through a microchannel of the invention is inversely proportional to the length of the longitudinal extent or path of the microchannel and the viscosity of the fluid and directly proportional to the product of the square of the hydraulic diameter of the microchannel, the square of the rotational speed of the platform, the average distance of the fluid in the channels from the center of the disk and the radial extent of the fluid subject to the centripetal force. Since the hydraulic diameter of a channel is proportional to the ratio of the cross-sectional area to cross-sectional perimeter of a channel, one can judiciously vary the depth and width of a channel to affect fluid flow (see Duffy et al., 1998, *Anal. Chem.* 71: 4669–4678 and co-owned and co-pending patent application U.S. Ser. Nos. 08/761,063, filed Dec. 5, 1996 and 08/768,990, filed Dec. 18, 1996, incorporated by reference).

For example, fluids of higher densities flow more rapidly than those of lower densities given the same geometric and rotational parameters. Similarly, fluids of lower viscosity flow more rapidly than fluids of higher viscosity given the same geometric and rotational parameters. If a microfluidics structure is displaced along the radial direction, thereby changing the average distance of the fluid from the center of the disc but maintaining all other parameters, the flow rate is affected: greater distances from the center result in greater flow rates. An increase or a decrease in the radial extent of the fluid also leads to an increase or decrease in the flow rate. These dependencies are all linear. Variation in the hydraulic diameter results in a quartic dependence of flow rate on hydraulic diameter (or quadratic dependence of fluid flow velocity on hydraulic diameter), with larger flow rates corresponding to larger diameters. Finally, an increase in the rotational rate results in a quadratic increase in the flow rate or fluid flow velocity.

Input and output (entry and exit) ports are components of the microplatforms of the invention that are used for the introduction or removal of fluid components. Entry ports are provided to allow samples and reagents to be placed on or injected onto the disk; these types of ports are generally located towards the center of the disk. Exit ports are also provided to allow products to be removed from the disk. Port shape and design vary according specific applications. For example, sample input ports are designed, inter alia, to allow capillary action to efficiently draw the sample into the disk. In addition, ports can be configured to enable automated sample/reagent loading or product removal. Entry and exit ports are most advantageously provided in arrays, whereby multiple samples are applied to the disk or to effect product removal from the microplatform.

In some embodiments of the platforms of the invention, the inlet and outlet ports are adapted to the use of manual pipettors and other means of delivering fluids to the reservoirs of the platform. In alternative, advantageous embodiments, the platform is adapted to the use of automated fluid loading devices. One example of such an automated device is a single pipette head located on a robotic arm that moves in a direction radially along the surface of the platform. In this embodiment, the platform could be indexed upon the spindle of the rotary motor in the azimuthal direction beneath the pipette head, which would travel in the radial direction to address the appropriate reservoir.

Another embodiment is a pipettor head adapted to address multiple reservoirs, either a subset of or all of the reservoirs on the platform surface. For embodiments where the pipettor head addresses a subset of the reservoirs, a single head may for example be composed of a linear array of pipette heads. For example, the entry ports of FIG. 1 might be addressed by indexing such a linear head in the direction transverse to the pipette tips. In other embodiments, pipette heads may be used which can simultaneously address all entry ports (for example, a 96-tip head). In these embodiments, there may be a distinction between sample entry ports—needed for the delivery of many samples—and reagent entry ports, through which larger volumes or reagent are delivered for use in reactions with all samples. A pipetting device that can simultaneously address all sample entry ports as well as reagent ports might consist of a standard multipipettor with a few added, large-volume delivery tips.

Also included in air handling systems on the disk are air displacement channels, whereby the movement of fluids displaces air through channels that connect to the fluid-containing microchannels retrograde to the direction of movement of the fluid, thereby providing a positive pressure to further motivate movement of the fluid.

Platforms of the invention such as disks and the microfluidics components comprising such platforms are advantageously provided having a variety of composition and surface coatings appropriate for particular applications. Platform composition will be a function of structural requirements, manufacturing processes, and reagent compatibility/chemical resistance properties. Specifically, platforms are provided that are made from inorganic crystalline or amorphous materials, e.g. silicon, silica, quartz, inert metals, or from organic materials such as plastics, for example, poly(methyl methacrylate) (PMMA), acetonitrile-butadiene-styrene (ABS), polycarbonate, polyethylene, polystyrene, polyolefins, polypropylene and metallocene. These may be used with unmodified or modified surfaces as described below. The platforms may also be made from thermoset materials such as polyurethane and poly(dimethyl siloxane) (PDMS). Also provided by the invention are platforms made of composites or combinations of these materials; for example, platforms manufactures of a plastic material having embedded therein an optically transparent glass surface comprising the detection chamber of the platform. Alternately, platforms composed of layers made from different materials may be made. The surface properties of these materials may be modified for specific applications, as disclosed in co-owned U.S. Pat. No. 6,063,589, issued May 16, 2000, and co-owned and co-pending patent application U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; and 09/315,114, filed May 19, 1999, the disclosures of each of which are explicitly incorporated by reference herein.

Preferably, the disk incorporates microfabricated mechanical, optical, and fluidic control components on platforms made from, for example, plastic, silica, quartz, metal or ceramic. These structures are constructed on a sub-millimeter scale by molding, photolithography, etching, stamping or other appropriate means, as described in more detail below. It will also be recognized that platforms comprising a multiplicity of the microfluidic structures are also encompassed by the invention, wherein individual combinations of microfluidics and reservoirs, or such reservoirs shared in common, are provided fluidly connected thereto. An example of such a platform is shown in FIG. 1.

Platform Manufacture and Assembly

Referring now to the Figures for a more thorough description of the invention, FIG. 1 shows an exploded oblique view of an example of a disc appropriate for the performance of 4 parallel cell based assays in quadruplicate. In this embodiment, platform 100 is composed of two layers, an upper reservoir layer 101 and a lower reservoir layer 199. In this example, the two layers are mirrored versions of one another except for two features described in detail below.

Assays are performed in the following general manner: A cell suspension is added to the disc and driven through channels and reservoirs under the influence of centripetal force produce by rotation of the platform. The suspended cells are distributed by flow across a porous support or filter, while the medium that carries the cells can traverse the pores of the support. The platform can also be sealed with a gas permeable membrane in the vicinity of the cell-retaining support, and the entire disc can be placed inside an incubator so that the trapped cells may attach and proliferate. Additionally media or reagents may be added through the same fluidic channels, for example exchanging nutrients or administering test compounds, dyes, and other compounds. All excess fluids are washed into waste reservoirs contained on the disc.

The disc depicted in FIG. 1 illustrates how a multiplicity of identical assays can be performed on a platform having repeating assay structures around the disc at a particular radius positioned at equivalent distances from the axis of rotation, as well as modifying the structures for placement at different radial positions. In FIG. 1, structure 103 (shown in more detail in FIG. 2) is repeated azimuthally around the platform layers 101 and 199. In this way, it is possible to fully cover the surface of the disc with microfluidics structures for performing assays. The maximum number of assays that may be performed will depend upon the volume of fluid that may be manipulated reproducibly, i.e., the minimum reproducible dimensions with which the disc may be fabricated, and the amount of hydrodynamic pressure required to drive small volumes of fluid through microchannels at convenient rotational rates. Taking these considerations into account, it is estimated that greater than 10,000 assays having volumes of 1–5 nL can be created in a circular platform having a 6 cm radius.

In FIG. 1, platform 100 is composed of at least 2 component layers. A fluidics layer 101 having features on one or both faces is used. In cases where both sides contain features, some features may be through-holes or vias connecting the fluidic networks, allowing for fluidic "crossovers" and three-dimensional flow from one side of the disc to the other. In such a case, a sealing film 198 (not shown) is preferably used to seal the channels on the "upper" side of the layer 101. The fluidic channels on the lower face of layer 101 must be sealed partially or completely through the use of one or more sealing layers or a second fluidics layer 199. The sealing layer may be a featureless material. It can also be composed of selectively-permeable material for the transmission of gases necessary for cell metabolism and elimination of gaseous waste products produced by that metabolism. Alternatively, the sealing layer may be replaced by a second fluidics layer with channels and reservoirs constructed to that channels and reservoirs on the two layers overlap. The embodiment shown in FIG. 1 is composed of two layers 101 and 199 that are mirrored versions that permit at all features to overlap on the two layers.

Platform 100 is preferably provided in the shape of a disc, a circular planar platform having a diameter of from about 10 mm to about 50 mm and a thickness of from about 0.1 mm to about 25 mm. Each layer comprising the platform preferably has a diameter that is substantially the same as the other layers, although in some embodiments the diameters of the different layers are not required to completely match. Each layer has a thickness ranging from about 0.1 mm to about 25 mm, said thickness depending in part on the volumetric capacity of the microfluidics components contained therein.

Figure 2:
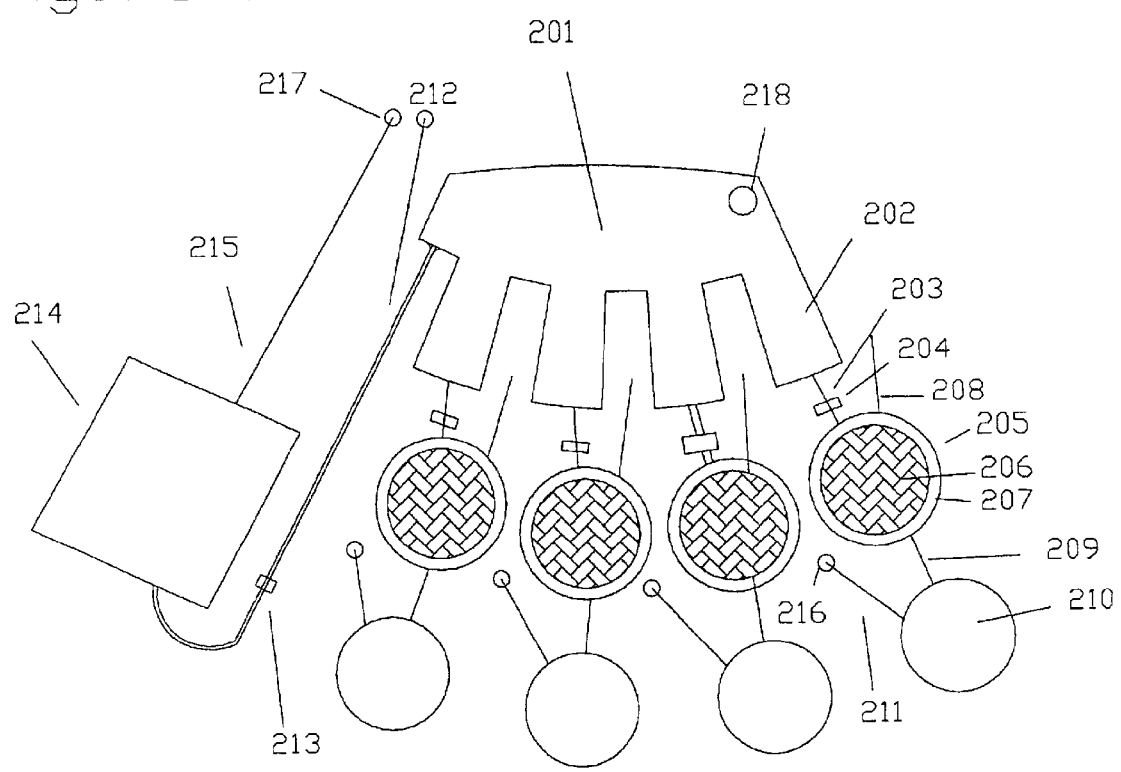
FIG. 2 depicts a detail of a structure for growing and assaying 4 populations of cells on the disc of FIG. 1.

Referring to FIG. 2, a single cell based assay structure is illustrated and will be described in the case of a single fluidics layer with sealing layer. The Figure illustrates structures necessary for the device's function. These include a fluid entry port 218 through which cell culture media, nutrient media, test compounds, dyes, and other components of cell based assays can be loaded. A distribution manifold 201 additionally has sub-volumes 202 that are used to divide the fluids into equal aliquots for delivery to the multiple incubation chambers. Also provided is an overflow channel 212 leading to an overflow reservoir 214; this may optionally pass through a capillary or physical valve 213. Air displaced as the fluid moves to the overflow chamber is vented via channel 215 and air-vent 217. Air displaced as fluid moves into the volumes 202 is vented through channels 203, chambers 205, cell support or filtering element 206 channels 211 and vents 216 in cases where no physical valve blocks channels 203. In some instances a physical valve may be placed such that it blocks 203 at position 204. In these instances, displaced air will either be expelled through the inward surface of fluid in subvolumes 202 or may be expelled via channels and vents not shown. The cell culturing chambers 205 may have channels 219 and air vents 220 and is optionally shaped to permit insertion of a cell support or filtering element 206, forming a leak-tight seal 207 with the surface of the platform through the use of solvent bonding, adhesive, or snap-in washers, screw-in elements, or a pressure seal between the layer 101 and sealing layer 199. Note that the cell support or filtering element 206 need not be placed in both layers 101 and 199.

Figure 3:
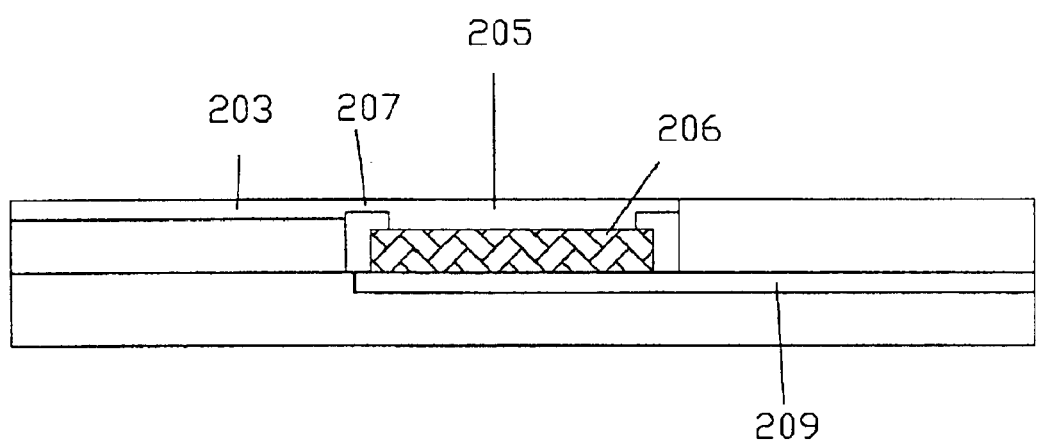
FIG. 3 is a cross-sectional view of the flow-through cell culturing chamber of the disc of FIG. 1.

The cell culturing chamber itself is shown in cross-section in FIG. 3. As shown, the upper layer 101 contains the inlet channel 203 and the cell support or filtering element 206, while layer 199 contains outlet channel 209 that communicates to overflow reservoir 210, air channel 211 and port 216. Channels 209 and 208 may also be coated with a hydrophobic coating material (e.g. PerFluorCoat, obtained from PFC MH-Series, Cytonix Corporation, Beltsville, Md. 20705). These coatings have the beneficial effect of preventing capillary action ("wicking") of fluids from one chamber to another, e.g., between overflow reservoir 210 and cell culturing chamber 205, when the disc is stationary, thus preventing waste or wash fluid from backflowing into the cell culturing chamber. They may also function as a temporary valve, inhibiting radially-outward flow much as a capillary valve does until disc rotation speed is sufficiently high to overcome surface forces.

To summarize the differences between 101 and 199, layer 101 contains the entry port 218, channel 203 and support 206 as well as sealings means 207, while layer 199 contains channel 209. Fluid passage between layers occurs at overlaps in reservoirs such as distributor manifold 201 and overflow reservoir 210 and at the culturing chamber 205. In alternative constructions, layer 101 may contain all of the features described above on its lower face which are radially inward, and inclusive, of cell culturing chamber 205. Layer 199 may then carry all structures that are radially outward of cell culturing chamber 205. Similarly, since the sequence of flow is to pass unidirectionally through cell culturing chamber 205, one layer may contain all components necessary for flow prior to reaching cell culturing chamber 205, while the other layer contains the remaining features for flow subsequent to cell culturing chamber 205.

In use, the disc functions as follows. A liquid sample containing cells, herein termed a cell suspension, is loaded through port 218. The disc is rotated at a first rate, and under centrifugation is distributed among sub-volumes 202. Fluid also passes into channel 212, but flow at this rotational speed is blocked, either by a capillary valve or physical valve 213. At a second rotational speed, the capillary forces at valve 213 are overcome and excess fluid flows into overflow chamber 214. Alternatively, a physical valve at 213 is opened, either at the first rotational speed or a second speed. Excess suspension is decanted into overflow chamber 214. At a third rotational speed, capillary valves 204 are overcome and suspension flows into cell culture chambers 205. Through use of a filter element 206 with sufficiently small pores, the hydraulic resistance of the filter is far greater than that of the channels; as result, the cell incubation chambers fills behind the filters, and then excess fluid can be spun through the filter into overflow chamber 210, if necessary.

The device may then be halted to allow the trapped cells to attach to cell support or filter element 206; incubation at 37° C. may follow, in order for the cells to multiply. Subsequent additions of nutrient media may be made using the same steps of addition, rotation, and valve actuation detailed above.

A reagent, for example a compound whose toxicity is being evaluated with the cells, is then added to port 218. Through repetition of the above steps, this second reagent enters cell culture chamber 205 and displaces the medium. The device may then be incubated once again to permit the adhered cells to absorb the reagent.

Further reagent additions may occur, such as indicator compounds; fixing stains which preferentially or differentially stain living or dead cells; color-generating or fluorescence-generating compounds that indicate the presence of specific metabolites generated by cultured cells; spectrophotometrically detect metabolites or altered forms of co-factors, and other detection methods known to those with skill in the art. The cells may be imaged in situ on the cell supports 206 and their morphology, number, or color determined. The eluent washed into chambers 210 may be spectroscopically or fluorometrically interrogated.

In some alternative embodiments of the device of FIG. 2, cell capturing elements 206 are not used. In such embodiments, hydrophobic coating of channel 209 may be used to retain fluids in the cell incubation chamber. Alternatively, channel 209 may be constructed so that it bends by 180 degrees, traces an inward radial path, and then bends 180 degrees again to trace an outward radial path toward chamber 210. If the radial position of the second bending is interior to the radially-inward edge of cell culture chamber 205, cell culture chamber 205 will remain filled with fluids as long as the connection of channel 209 to chamber 210 is designed to prevent siphoning of fluids.

It will be understood that the disc may be extended to multiple samples of cells and multiple kinds of assays through the combination of the individual cell-culturing chambers disclosed herein and the liquid-handling capabilities known in the art, for example as disclosed in co-owned U.S. Pat. No. 6,063,589, issued May 16, 2000, and co-owned and co-pending patent application U.S. Ser. Nos. 08/761,063, filed Dec. 5, 1996; 08/768,990, filed Dec. 18, 1996; 08/910,726, filed Aug. 12, 1997; 08/995,056, filed Dec. 19, 1997; and 09/315,114, filed May 19, 1999, the disclosures of each of which are explicitly incorporated by reference herein.

Figure 4:
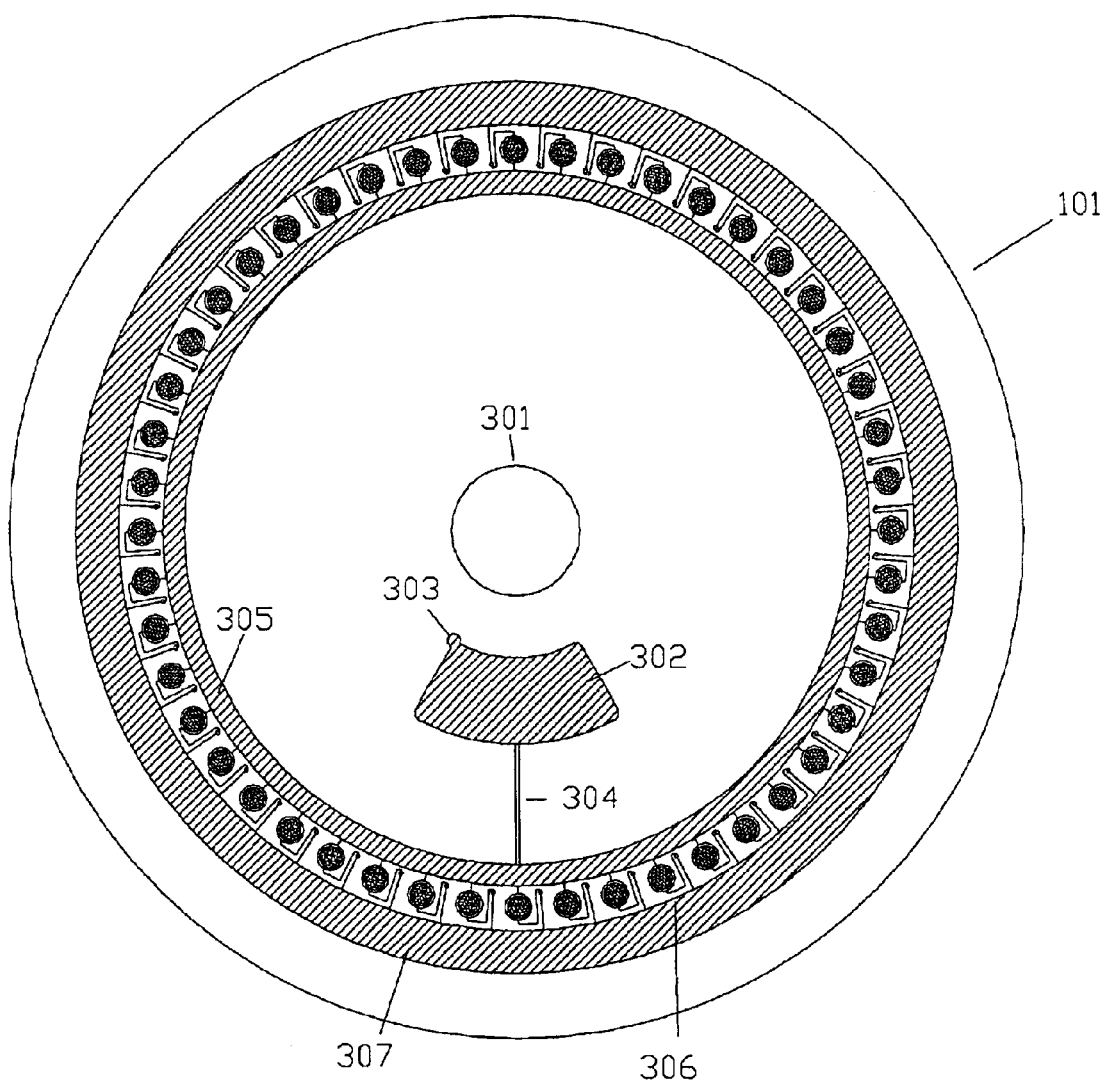
FIG. 4 illustrates an alternate construction of the disc of FIG. 1 for the performance of 48 cell-based assays.

Another alternative embodiment is shown in FIG. 4. The disc of FIG. 4 is designed for the performance of 48 identical assays on identical cell populations, and hence is appropriate for large numbers of "repeats". In FIG. 4, platform 300 is composed of at least 2 component layers, a fluidics layer 101 and sealing layer 199 as discussed above. Fluidics layer 101 contains a central hole or mounting features 301 for attachment to the rotary spindle of the manipulation device. It further comprises a reagent reservoir 303 accessed by a port 302. This reservoir is connected by channel 304 to a distribution manifold 305. The distribution manifold is further connected to the individual assay structures 306. Fluids that pass through structures 306 are collected in waste reservoir 307.

Figure 5:
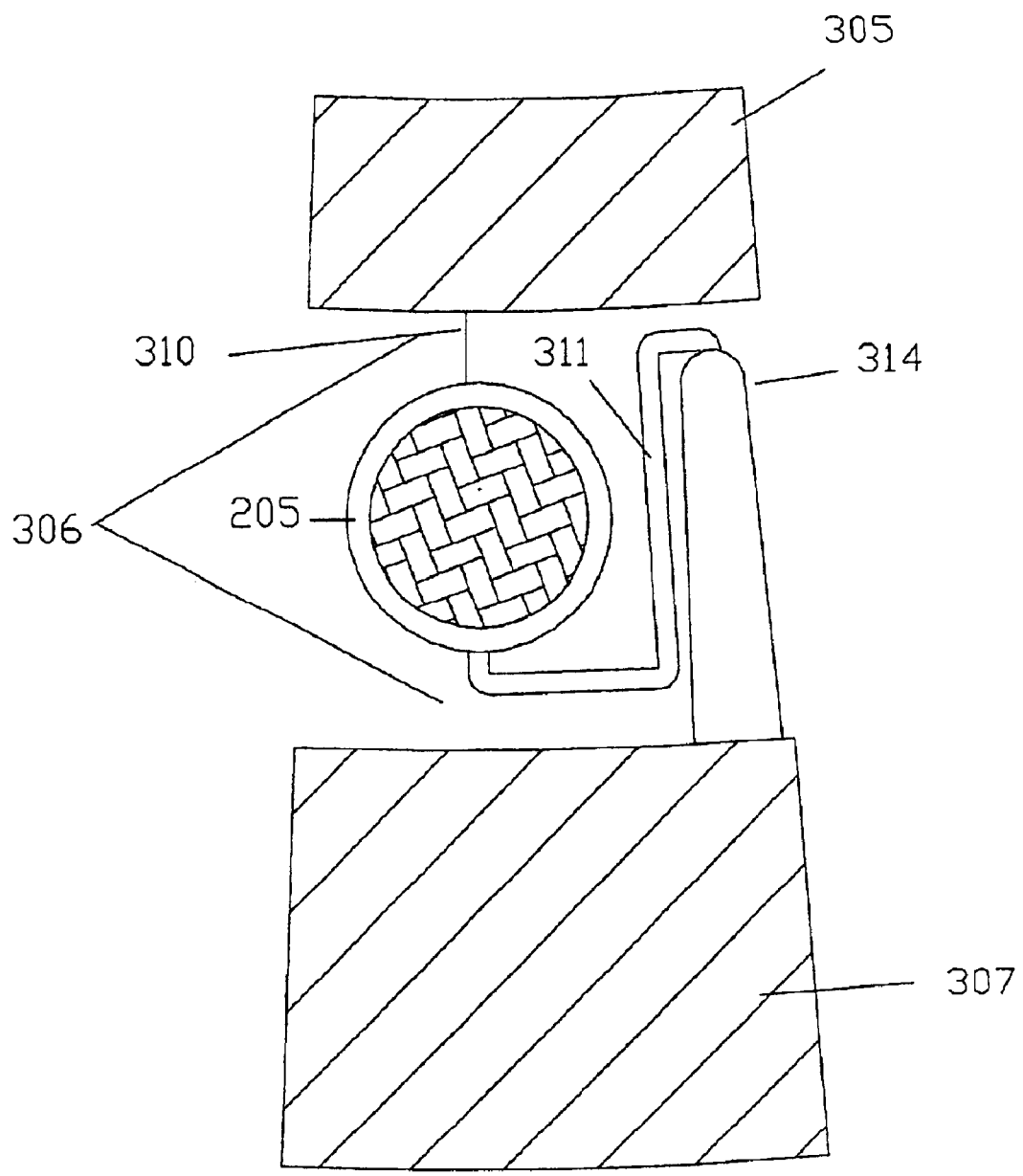
FIG. 5 is a detail of a single assay microstructure of the disc of FIG. 4.

An individual cell-based assay structure comprising the disc shown in FIG. 4 is set forth in FIG. 5 and will be described in the case of a single fluidics layer with sealing layer. Referring to FIG. 5, a variety of features necessary for device function are shown. These include the fluid distribution manifold 305 that is fluidly connected to cell assay structure 306, which is comprised of cell culture chamber 205, channels 310 and 311 and passage 314. Manifold 305 is fluidly connected to channel 310; the cell culture chamber 205 is shown here with a cell-retaining filter 206. Cell culture chamber 205 is connected to waste reservoir 307 through a "U-channel" 311 as described above. Channel 311 passes through a passage 314, which is at least twice as deep and twice as wide as the channel itself. A single air-vent (not shown) in the waste reservoir 307 is sufficient for the removal of displaced air.

Figure 6:
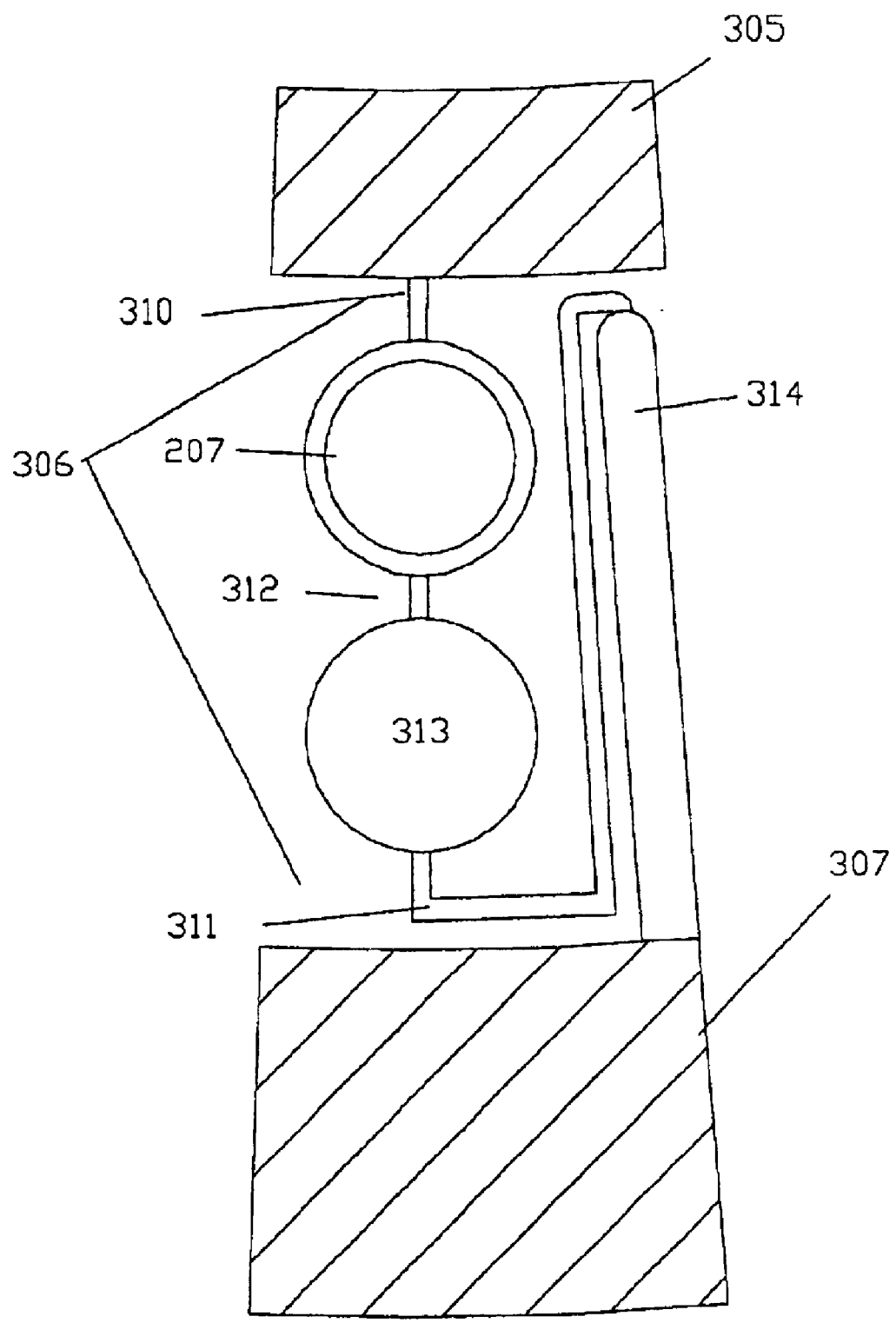
FIG. 6 is an alternate construction of the microstructure of FIG. 5.

An alternative construction of the cell incubation structure 306 is shown in FIG. 6. This structure additionally contains an optical detection cuvette 313 connected via channel 312 to cell culture chamber 205. The channel then leads from detection cuvette 313 to waste reservoir 307, via passage 314.

In use, these embodiments of the disc function as follows. First, a liquid sample containing cells, herein termed a cell suspension, is loaded through port 303. The disc is rotated at a first rotational speed, and the cell suspension is displaced into manifold 305. By using channels 310 with very small diameters (10–250 microns), fluid resistance leading to the incubation chambers is large, such that fluid is distributed throughout the annular manifold 305. As rotation continues, the cell suspension flows into the plurality of cell culture chambers 205 and, in some embodiments, detection cuvette 313. In some embodiments, a cell-trapping filter retains the cells in chamber 205, leaving the detection cuvette free of cells. In other embodiments that do not use filtering elements, the surface of 313 may be treated in manufacture to minimize or eliminate cell attachment. As a result, cells allowed to settle by gravity onto the surface of 313 will not proliferate. In alternative embodiments, the channel 312 may be treated to be hydrophobic, preventing the first cell suspension solution from passing into chamber 313 at a first rotational speed; the cell suspension medium will pass through 312 to 313 and thence 307 at a second, higher rotational speed under conditions whereby the cells do not settle in detection cuvette 313. In cell culture chamber 205, however, cells are allowed to attach and grow. Incubation at 37° C. follows, in order for the cells to attach and multiply. Subsequent additions of nutrient media may be made using the same steps of addition, rotation, and valve actuation detailed above.

The shape of channel 311 and presence of passage 314 insure that cell culture chamber 205 and detection chamber 313 (where present) always remain filled with fluid. When fluid first passes through cell culture chamber 205 and thence into detection chamber 311, the fluid is driven by the hydrostatic pressure of the fluid in cell culture chamber 205 and remaining in manifold 305 to travel radially inward in channel 311 and thence into channel 314. Because channel 314 is sized significantly larger than channel 311, the emergent fluid will "drip", forming droplets, which are driven under centrifugation into overflow reservoir 307 more rapidly than fluid can flow through the channels and chambers of the structure. In particular, channel 311 presents the largest "resistance" to the flow of liquid due to its significant length and small diameter, while 314 provides less resistance and is sized large enough for the formation of droplets, rather than a continuous flow. As a result, when all fluid in manifold 305 has been pumped outward into channel 310, flow will cease when the meniscus of fluid entering the structure 306 is at the radial position of the opening of channel 311 into channel 314. If channel 311 were used without channel 314, that is, channel 311 continued out to be fluidly connect with overflow reservoir 307, fluids would be "siphoned" through the cell culturing chamber, eventually emptying it and detection chamber 313 (if present) of all fluid.

A second reagent, for example a compound whose toxicity is being evaluated with the cells, is now added to port 303. Through repetition of the above steps, this second reagent enters cell culture chamber 205 and displaces the cell culture medium therein. The device may then be incubated once again such that the adherent cells may absorb or otherwise interact with the compounds of the reagent mix.

Further reagent additions may occur, for example, of indicator compounds, such as fixing stains that preferentially or differentially stain living or dead cells; color-generating or fluorescence-generating compounds that indicator the presence of specific metabolites generated by cultured cells; and other detection means known to those with skill in the art. The cells may be imaged on the cell supports 206 and their morphology, number, or color determined. The eluent washed into detection chamber 313 may be spectroscopically or fluorometrically interrogated.

Alternate constructions of the discs of FIGS. 4–6 may include, for example, overflow channels and reservoirs as discussed in co-owned U.S. Pat. No. 6,063,589, issued May 16, 2000, the disclosure of which are explicitly incorporated by reference herein., that permits the use of imprecisely metered volumes of fluid. It will also be understood by those with skill in the art that the platform shown in FIGS. 4 through 6 can be constructed to permit multiple assays on multiple cell populations to be performed. This may be accomplished, for example, by providing multiple reservoirs 303 and multiple manifolds 305. For example, a disc that would be used to run 4 independent assays on 4 populations of 12 cell incubations would comprise 4 reservoirs 303 connected to four manifolds 305. Each manifold 305 would in turn be fluidly connected to 12 cell assay structures 306.

Figure 7:
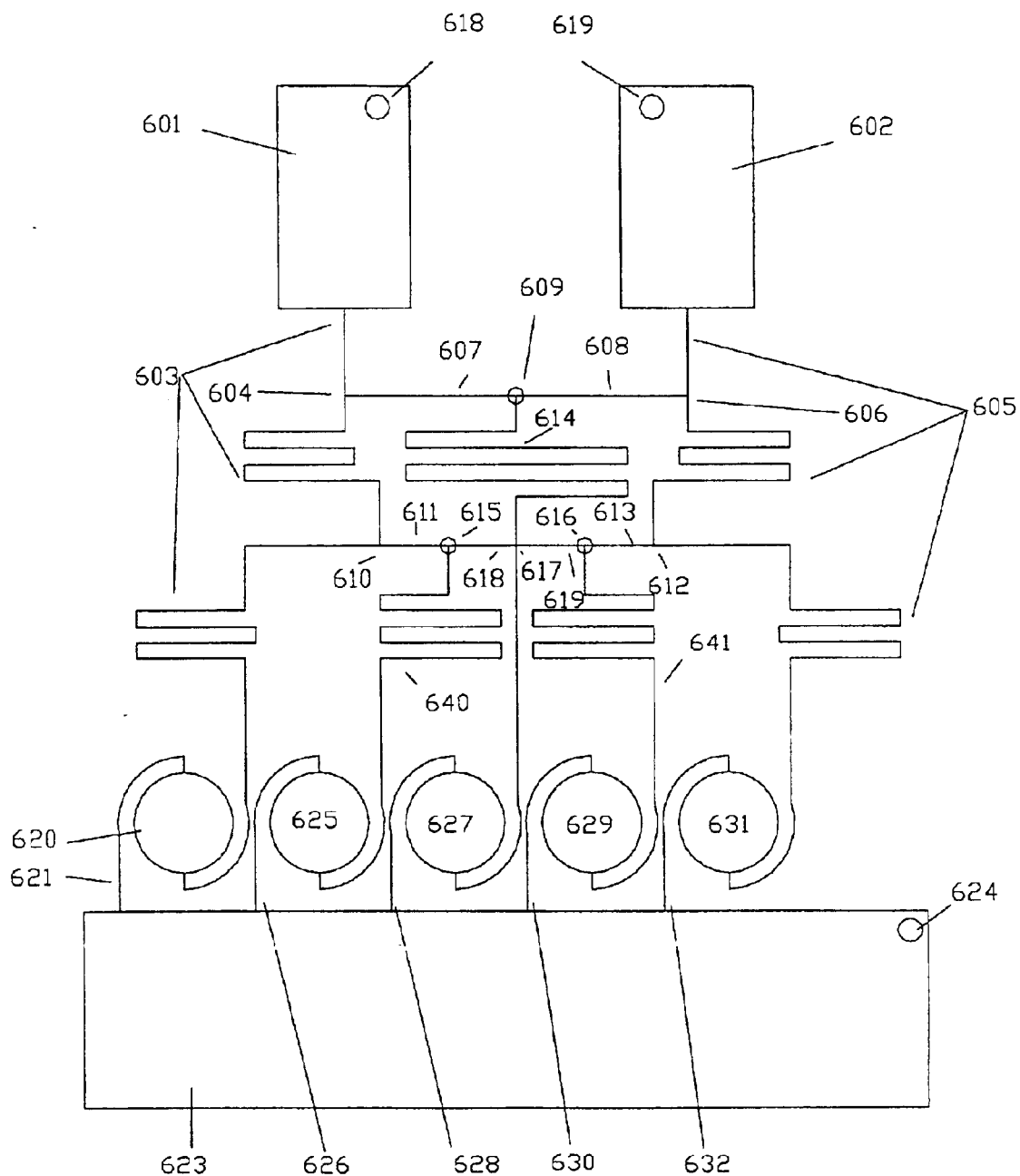
FIG. 7 is a version of the disc of FIG. 1 designed for the delivery of a dilution series to the chambers.

FIG. 7 is a third alternative embodiment, shown schematically. In this Figure, a microfluidic network (collectively termed "a branching dilution microchannel") for the creation of a dilution series is illustrated and is part of a larger network of structures used for cell based assays. Reservoirs 601 and 602 are accessed by entry ports 618 and 619 respectively. Fluid channel 603 exits reservoir 601 and is split into two components at T-junction 604, a portion of which continues to further T-junctions and a portion of which, 607, terminates at capillary junction 609. Similarly, reservoir 602 leads to channel 605, which is split at T-junction 606; one arm of the split channel continues to further T-junctions, while the other arm, 608, terminates at the capillary junction 609. Following channel 603 past T-junction 604, it is again split at T-junction 610 into a portion which leads to cell culturing chamber 620; the other portion, 611, terminates at capillary junction 615. Similarly, channel 605 leads to T-junction 612, where it is split into channel 613, which terminates at capillary junction 618 and a portion that continues to cell culturing chamber 631. The capillary junctions 609, 615, and 616 all are fluidly connected to channels 614, 640, and 641, respectively. Channels 640 and 641 lead respectively to cell culturing chambers 625 and 629. Channel 614 is further split at a 4-armed junction 617 into 3 channels: A continuation of 614, which leads to cell culturing chamber 627, and side channels 618 and 619 which terminate at capillary junctions 615 and 616, respectively.

The cell culture chamber 620 is further connected to channel 621 that emerges radially-inward of the chamber and then leads to waste reservoir 623; an air vent 624 is provided for the removal of displaced air. Cell culture chambers 625, 627, 629, and 631 are likewise connected via channels 626, 628, 630, and 632 to the waste reservoir 623.

The fluid channels described here are preferably sized such that the residence time within the channel of a fluid element under centrifugal flow is sufficient to allow diffusional mixing across the diameter of the channel. The design of such mixing elements is defined in co-owned and co-pending U.S. application Ser. No. 09/595,239, filed Jun. 16, 2000, incorporated by reference herein.

The disc is used as follows. Cell suspensions are loaded into both reservoirs 601 and 602. Under the influence of rotation, the suspensions are driven into channels 603 and 604. As they are pumped via centrifugation, the fluids divide and recombine. Since they are identical fluids, identical cell suspension is delivered to all five incubation chambers. In an alternative construction, separate delivery means to the cell culture chambers may be provided, for example, in the form of channels and entry ports leading to the chambers, so that they are individually loaded; or a separate distribution reservoir, potentially on the other face of the microplatform or on another microplatform connected to that shown here. The manner in which multiple liquids are distributed to an arbitrary position on the microdevice by using a three-dimensional network of channels is more fully disclosed in U.S. Serial No. 60/204,272, filed May 15, 2000, U.S. Ser. No. 09/858,318, filed May 15, 2001 (Attorney Docket No. 95,1408-GGG, and International Application No. PCT/US01/158,43, filed May 15, 2001, Attorney Docket No. 95,1408-HHH, incorporated by reference herein.

Cells are allowed to attach to the surfaces of the culturing chambers, and the entire platform can be placed inside an incubator at an appropriate temperature. Exchange of nutrient medium may be accomplished as described for the initial distribution of cellular suspension.

The disc is then used to create a series of mixtures of two solutions in which the ratio of solutions is varied. If one solution contains a compound suspected of some biological effect on the cells and the other is a buffer or cell culture medium, the series of solutions may be called a dilution series. Fluid A is pipetted through 618 into reservoir 601, while fluid B is pipetted through port 619 into reservoir 602. The disc is rotated at a first rotational rate. The fluids enter channels 603 and 605. Fluid A reaches the T-junction 604, at which point a portion of the fluid continues down channel 603 and a portion flows into channel 607. Similarly, fluid B splits at 606 into channels 605 and 608. The portion of Fluid A present in 607 reaches capillary junction 609, as does the fluid B present in 608. As the disc is spun to overcome capillary force at 609, the fluids are brought together and flow into meandering mixing channel 610. Mixing in this channel is described in co-owned and co-pending U.S. application Ser. No. 09/595,239, filed Jun. 16, 2000, incorporated by reference herein. The fluid in channel 614, after sufficient time for diffusional mixing in the channel, arrives at junction 617 with a volume fraction of A equal to 0.5 and B equal to 0.5, i.e., the fluids A and B are "mixed". The mixed fluid arriving at 617 may be denoted as fluid C1.

Fluid C1 is split into 3 streams at junction 617. A portion of that mixed liquid C1 now mixes with the original A solution which has been directed by channel 603 to junction 610 and channel 611, by passing through capillary junction 615. This fluid C2 in channel 640 has volume fraction of A of 0.75 and B of 0.25. Similarly, the fluid in 641 has volume fraction of A of 0.25 and B of 0.75.

As shown, the fluidic network delivers 5 concentrations of A—1.0,0.75,0.5,0.25,0.0—to the cuvettes 620, 625, 627, 629, and 631, respectively. In order to achieve these ratios, the flow rates of the two fluids entering any mixing channel 614, 640, and 641 must be equal. This is assured by the diameter of the channels, as fluid flow is controlled by the fluidic impedances of the various mixing channels.

It will be understood that the process of dividing and recombining channels illustrated may be continued indefinitely. One further splitting and recombination in the manner shown would lead to a total of 9 concentrations of A: 1.0, 0.875, 0.75, 0.625, 0.5, 0.375, 0.125, 0.125, and 0.0.

The following Examples are intended to further illustrate certain preferred embodiments of the invention and are not limiting in nature.

EXAMPLE 1

The disc disclosed in FIGS. 1–3 was used in order to illustrate filtration of small particles using a two-level disc construction.

The Microsystems platform was prepared as follows. The fluidic layers were manufactured through machining of acrylic using computer/numerical code machining using a Light Machines VMC5000 milling machine running Light Machines "Benchman" software (Light Machines Corporation, Manchester, N.H.).

The particle-capturing cell growth substrate 206 comprised a Whatman Microfibre glass filter with a 2.7 $\mu$m diameter pore size. In some experiments these were substituted with Whatman Cyclopore polycarbonate membranes having 3.0 $\mu$m diameter pores. This filtering element was sealed into the cell culturing chamber 205 along its circumference 207 using solvent bonding using dimethyl chloride solvent, epoxy, and nail polish for different experiments.

In some experiments, channel 209 was coated with a hydrophobic coating, PerFluorCoat (PFC MH-Series, Cytonix Corporation, Beltsville, Md. 20705).

The two discs were affixed to one another using double-sided tape after alignment.

The dimensions of the platform used for these assays were as follows. The overall platform diameter was 12 cm. Fluidics layer 101 was 12 cm in diameter and 1.5 mm thick, as was layer 199. The distribution manifold 201 ranged from about 1.5 cm radius to 2.5 cm and subtended an angle of 67 degrees. The manifold was about 1 mm deep, and the sub-volumes 202 were designed to hold 40 $\mu$L. The overflow channel 212 had a width and depth of 0.5 mm and there was a capillary junction at 213 that was wider and deeper than channel 212. The cell culturing chamber 205 had a diameter of 7 mm and a volumetric capacity of 30 $\mu$L. Channels 203 and 209 were 0.5 mm wide and 0.5 mm deep. Of these channels, channel 203 was present on layer 101, while channel 209 was present on layer 199. In this way, fluid was forced to pass through the filtering element 206.

Experiments were performed using fluorescent latex beads of a variety of sizes, ranging from about 4.5 to about 6 $\mu$m. Bead solutions containing approximately 0.25% beads (by volume) were added to entry port 218 and the device was spun to 300 rpm. At this rotational speed, capillary valve 213 allowed excess fluid to flow into overflow reservoir 214. Fluid in the subvolumes 202 were retained by capillary valves 204 until the rotational rate was increased to 500 rpm, at which point they flowed into the chambers 205. Spinning at 1000 rpm drove fluid through support 206. The device disc was then placed under a Nikon fluorescence microscope. Comparison of the number of beads detected in cell culture chamber 205 and overflow reservoir 210 showed that more than 90% of the beads were retained by filter 206.

EXAMPLE 2

Figure 8:
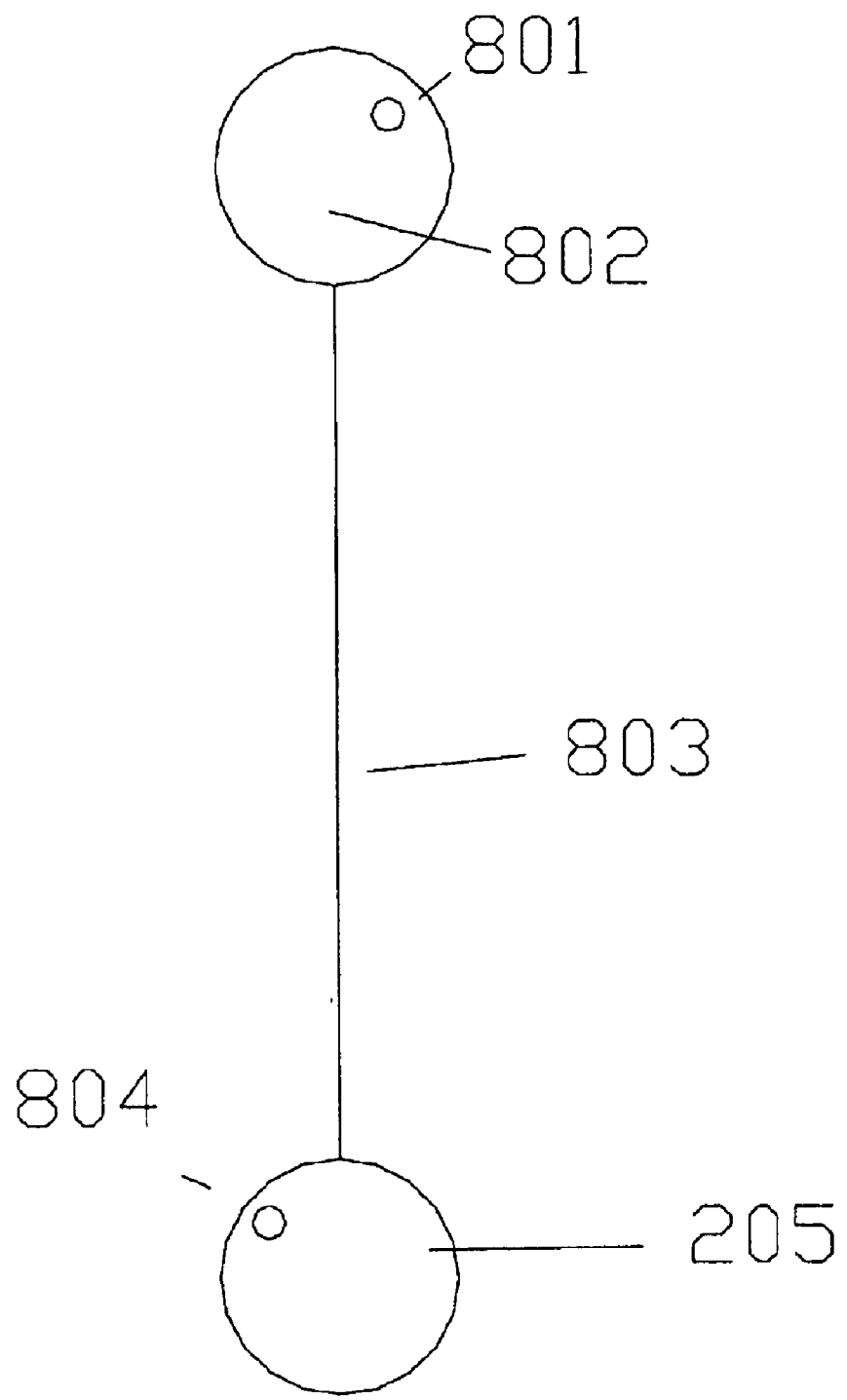
FIG. 8 is a version of the microstructure of FIG. 2 used for a viability assay.

The disc shown in FIG. 8 was used for a cell viability and staining assay. This disc is a simplified version that illustrates that cells may be loaded onto, cultured, and maintained within the structures of a microfluidic disc.

The assay structure consists of a fluid addition port 801 and channel 802 with allows fluids to be added to cell culturing chamber 205. There is also an air displacement channel 803 and vent 804 for the removal of displaced air. Cell culturing chamber 205 is connected via channel 805 to a waste reservoir 806. There is also an air displacement channel 807 and vent 808 for the removal of displaced air. Cell incubation chamber was designed to hold approximately 40 $\mu$L of liquid.

The disc was fabricated using CNC machining, as described above, and assembled using double-sided tape. A further passivation step, in which parylene was conformally deposited through chemical vapor deposition, was explored, though found unnecessary.

The experiments were performed as follows. A mammalian cell culture of 3T3 Swiss mouse fibroblast cells was grown using conventional methods. The cell culture was harvested and diluted to 70 cells/$\mu$L. The cells were then loaded into multiple structures comprising cell culturing chamber 205 via port 801, chamber 802 while the air port 808 was covered, to prevent liquid from flowing into 806. The disc was then placed in an incubator at 37° C. and incubated for 3 hours. It was removed from the incubator and the vent 808 uncovered. The cell culture medium was spun out at a rotational speed of 1000 rpm into the waste chamber 806. Live/Dead reagents (Molecular Probes) were then added to cell culture chamber 205. These reagents are fluorogenic esterase substrates, which, upon diffusion into the cell, are cleaved by nonspecific intracellular esterases, producing fluorescent compounds. As a result, living cells may be fluorescently imaged. The fluorscent compounds rapidly diffuse through the broken cell walls of dead cells, making it possible to distinguish between live and dead cells. The disc was incubated at 37° C. for 30 minutes and examined under a microscope.

Figure 9:
FIG. 9 is an image of stained cells showing viability and proliferation in the disc of the invention (FIG. 8).

Observing the surface of cell culture chamber 205, cell counts showed that the number of cells had increased during the incubation, and that the dye had been fixed; an exemplary image is shown in FIG. 9. This result shows that the cells were alive when the dye was added to the cell culture chamber 205. Furthermore, the experiment shows that assays that had attached to the surface of cell culture chamber 205 remained attached even under centrifugation at 1000 rpm.

EXAMPLE 3

In this example, a simplified device consisting solely of a cell culturing chamber with an entry port and air displacement channel and vent was used to demonstrate the ability to culture cells within a chamber on the device and to detect metabolic processes through the use of an indicating chemistry.

In this assay, the layer 101 was fabricated and assembled as in the first two Examples. A cell culture was assayed for cell number using a hemacytometer and diluted with nutrient medium/alamarBlue solution to concentrations of $2.5 \times 10^3$ cells/100 µL, $5 \times 10^3$ cells/100 µL, $7.5 \times 10^3$ cells/100 µL, and $10 \times 10^3$ cells/100 µL. The alamarBlue/nutrient solution was 10% by weight alamarBlue reagent (Accumed). AlamarBlue reagent is blue in its unreduced, native state. It can function as an oxidizing agent in metabolic pathways, and thereby be reduced to a red form which is also fluorescent.

Figure 10:
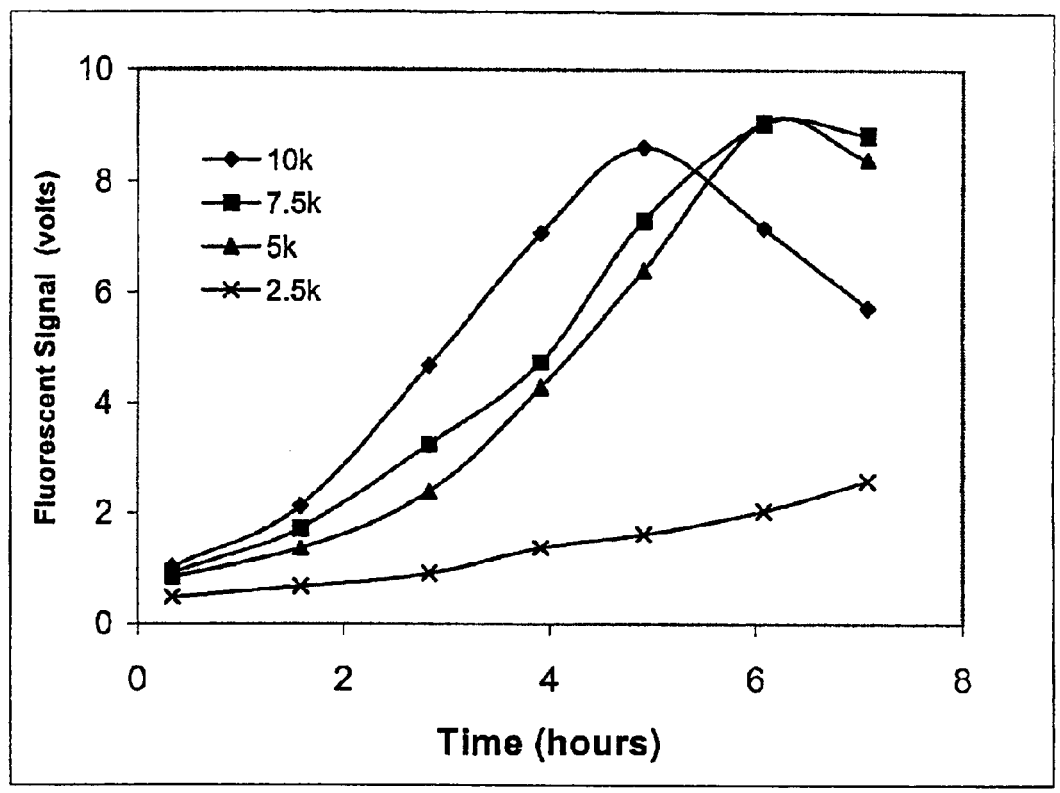
FIG. 10 is a time-course of fluorescence data from cells cultured within cell incubation chambers of the disc using alamarBlue reagents.

FIG. 10 illustrates a the fluorescence reading for the various cell populations pipetted into optical cuvettes of the disc. The difference in cell numbers is readily detected at the time of cell plating ($t_0$). Fluorescence increases with time, indicating a build-up of reduced product; and the exponential nature of the initial increase shows that the number of cells is increasing in each trace, that is, the cells are living and multiplying. The details of the shapes of the curves at long time are unimportant for this assessment of viability, and are due to exhaustion of reagent and breakdown of the fluorescent product.

This example demonstrates not only the viability of cells within chambers of the invention, but the ability to monitor their state in real time.

It should be understood that the foregoing disclosure emphasizes certain specific embodiments of the invention and that all modifications or alternatives equivalent thereto are within the spirit and scope of the invention.

We claim:

1. A centripetally-motivated microsystems platform comprising:
   a) a rotatable platform comprising a substrate having a surface comprising a one or a multiplicity of microfluidics structures embedded in the surface of the platform, wherein each microfluidics structure comprises
      i) a distribution manifold,
      i) one or a plurality of cell culture chambers adapted or treated to permit cell attachment and growth, and
      ii) one or a plurality of overflow reservoirs
   wherein each of said cell culture chambers is fluidly connected to the distribution manifold and to at least one of the plurality of overflow reservoirs microchannels, and wherein the platform further comprises
   b) a distribution manifold overflow reservoir, wherein the overflow reservoir is fluidly connected to the distribution manifold by a microchannel that makes a fluid connection with the distribution manifold at a position on the manifold proximal to the axis of rotation, and wherein fluid within the microchannels of the platform is moved through said microchannels by centripetal force arising from rotational motion of the platform for a time and a rotational velocity sufficient to move the fluid through the microchannels.

2. A microsystems platform according to claim 1, wherein each of the plurality of cell culture chambers further comprises a cell support or filtering element.

3. A microsystems platform according to claim 1, further comprising a plurality of detection chambers, wherein each detection chamber is fluidly connected by microchannels to one of the plurality of cell culture chambers and one of the plurality of overflow reservoirs, and is positioned on the platform between the cell culture chamber and the overflow reservoir.

4. A microsystem platform of claim 3 wherein the detection reservoirs are optically transparent.

5. A microsystem platform of claim 1 wherein the distribution manifold has a volumetric capacity of from about 1 nL to about 500 µL.

6. A microsystem platform of claim 1 wherein each cell culture chamber has a volumetric capacity of from about 2 nL to about 1000 µL.

7. A microsystem platform of claim 3 wherein each detection reservoir has a volumetric capacity of from about 2 nL to about 1000 µL.

8. A microsystem platform of claim 2 wherein the cell support or filtering element is a porous membrane having a pore size that prevents passage of cultured cells therethrough.

9. A microsystem platform of claim 1 comprising from about 24 to about 10,000 microfluidics structures.

10. A microsystem platform of claim 1 that is a circular disk having a radius of about 1 to about 25 cm.

11. The microsystem platform of claim 1, wherein the microsystem platform is constructed of a material selected from the group consisting of an organic material, an inorganic material, a crystalline material and an amorphous material.

12. The microsystem platform of claim 11, wherein the microsystem platform further comprises a material selected from the group consisting of silicon, silica, quartz, a ceramic, a metal or a plastic.

13. The microsystem platform of claim 1, wherein the microsystem platform has a thickness of about 0.1 to 100 mm, and wherein the cross-sectional dimension of the microchannels embedded therein is less than 1 mm and from 1 to 90 percent of said cross-sectional dimension of the platform.

14. A microsystem platform of claim 3 wherein each detection chamber has a volumetric capacity of from about 2 nL to about 1000 µL.

15. A microsystems platform of claim 1, wherein each of the microchannels fluidly connected to the cell culture chamber and overflow reservoir is coated with a hydrophobic coating.

16. The microsystem platform of claim 1, comprising a first layer and a second layer, wherein the first layer comprises a distribution manifold and cell culture chambers, and the second layer comprises microchannels, distribution manifold overflow reservoir, detection chambers and overflow reservoirs, wherein the distribution manifold and cell culture chambers in the first layer are fluidly connected by the microchannels, distribution manifold overflow reservoir, detection chambers and overflow reservoirs in the second layer when the first layer is in contact with the second layer.

17. A centripetally-motivated fluid micromanipulation apparatus that is a combination of
   a microsystem platform according to claim 1, and
   a micromanipulation device, comprising a base, a rotating means, a power supply and user interface and operations controlling means, wherein the rotating means is operatively linked to the microsystem platform and in rotational contact therewith
   wherein a volume of a fluid within the microchannels of the platform is moved through said microchannels by centripetal force arising from rotational motion of the platform for a time and a rotational velocity sufficient to move the fluid through the microchannels.

18. The apparatus of claim 17, wherein the rotating means of the device is a motor.

19. The apparatus of claim 17, wherein the device comprises a rotational motion controlling means for controlling the rotational acceleration and velocity of the microsystem platform.

20. An apparatus of claim 17 wherein the micromanipulation apparatus further comprises an optical detector that measures absorbance, fluorescence, epifluorescence or chemoluminescence.

21. An apparatus of claim 17 wherein the micromanipulation apparatus further comprises a scanning, imaging, or confocal microscopy detector.

22. An apparatus of claim 17 wherein the micromanipulation apparatus further comprises a radiometric detector.

23. An apparatus of claim 20, wherein the detector is brought into alignment with the collection chamber on the platform by rotational motion of the microsystem platform.

24. The apparatus of claim 23, wherein the detector is an optical detector comprising a light source and a photodetector.

25. A method for performing a cell-based assay, comprising the steps of:
   a) applying a volume of a fluid comprising a cell suspension to the distribution manifold of a microsystem platform of claim 1 when the platform is stationary,
   b) rotating the platform at a first rotational speed wherein a portion of the suspension occupies one or a plurality of subvolumes of the distribution manifold,
   c) rotating the platform at a second rotational speed that is higher than the first rotational speed wherein the portion of the cell suspension that does not occupy one or a plurality of subvolumes of the distribution manifold is motivated from the distribution manifold to the cell suspension overflow reservoir;
   d) rotating the platform at a third rotational speed that is higher than the second rotational speed to motivate fluid flow from the subvolumes of the distribution manifold into one or each of a plurality of cell culture chambers;
   e) incubating the platform for a time and under conditions for the cells to attach to the cell culture chamber and grow;
   f) applying a volume of a reagent solution to the distribution manifold of a microsystem platform of claim 1 when the platform is stationary,
   g) rotating the platform at a first rotational speed wherein a portion of the reagent solution occupies one or a plurality of subvolumes of the distribution manifold,
   h) rotating the platform at a second rotational speed that is higher than the first rotational speed wherein the portion of the reagent solution that does not occupy one or a plurality of subvolumes of the distribution manifold is motivated from the distribution manifold to the cell suspension overflow reservoir;
   i) rotating the platform at a third rotational speed that is higher than the second rotational speed to motivate fluid flow from the subvolumes of the distribution manifold into one or each of a plurality of cell culture chambers;
   j) incubating the platform for a time and under conditions for the cells to interact with the reagent and produce a detectable product; and
   k) detecting a product of the biological or biochemical reaction.

26. A method according to claim 22, wherein the reagent is a drug lead compound.

* * * * *